United States Patent
Von Schuckmann (10) Patent No.: US 11,766,529 B2
(45) Date of Patent: Sep. 26, 2023

(54) DEVICE FOR INHALING POWDERY SUBSTANCES

(71) Applicant: Alfred Von Schuckmann, Kevelaer (DE)

(72) Inventor: Alfred Von Schuckmann, Kevelaer (DE)

( * ) Notice: Subject to any disclaimer, the term of this patent is extended or adjusted under 35 U.S.C. 154(b) by 617 days.

(21) Appl. No.: 16/325,612

(22) PCT Filed: Aug. 10, 2017

(86) PCT No.: PCT/EP2017/070342
§ 371 (c)(1),
(2) Date: Feb. 14, 2019

(87) PCT Pub. No.: WO2018/036836
PCT Pub. Date: Mar. 1, 2018

(65) Prior Publication Data
US 2019/0269866 A1    Sep. 5, 2019

(30) Foreign Application Priority Data

Aug. 25, 2016  (DE) ...................... 20 2016 104 666.1
Jan. 20, 2017  (DE) ...................... 20 2017 100 316.7
Apr. 20, 2017  (DE) ...................... 20 2017 102 334.6

(51) Int. Cl.
*A61M 15/00*    (2006.01)
*A61M 11/00*    (2006.01)

(52) U.S. Cl.
CPC ........ *A61M 15/0041* (2014.02); *A61M 11/00* (2013.01); *A61M 11/003* (2014.02);
(Continued)

(58) Field of Classification Search
CPC ............ A61M 2205/582; A61M 11/00; A61M 11/08; A61M 15/00; A61M 15/009;
(Continued)

(56) References Cited

U.S. PATENT DOCUMENTS 1,525,665 A * 2/1925 Slover .................... A45D 33/26
                                                    132/297
1,541,451 A * 6/1925 Wallace ............... A45D 33/006
                                                    359/872
(Continued)

FOREIGN PATENT DOCUMENTS

GB    2 407 042 A    4/2005
GB    2 439 205 A    12/2007
(Continued)

OTHER PUBLICATIONS

International Search Report of PCT/EP2017/070342, dated Nov. 16, 2017.

*Primary Examiner* — Justine R Yu
*Assistant Examiner* — Alexander Morales
(74) *Attorney, Agent, or Firm* — Collard & Roe, P.C.

(57) ABSTRACT

A device for inhaling powdery substances contained in capsules has a housing, a capsule receiver, a closing cover, a mouth piece, and a closure cap. The closure cap is designed to cover simultaneously the mouthpiece, closing cover and capsule receiver, wherein the closure cap, mouthpiece and closing cover are hinged in a pivoting manner. Two pivot axes, which are different but run in the same direction, are formed, which, in respect of a side view in which geometric axes of the pivot axes are represented in the form of points, are arranged next to each other and on a same side of the capsule receiver. In a usage state of the device, the first pivot axis is arranged closer to the capsule receiver. The closing cover and the mouthpiece can be pivoted about the first pivot axis and only the closure cap can be pivoted about the second pivot axis.

10 Claims, 12 Drawing Sheets

(52) U.S. Cl.
CPC .......... *A61M 15/00* (2013.01); *A61M 15/003* (2014.02); *A61M 15/0023* (2014.02); *A61M 15/0026* (2014.02); *A61M 15/0028* (2013.01); *A61M 15/0035* (2014.02); *A61M 15/0001* (2014.02); *A61M 15/0021* (2014.02); *A61M 15/0025* (2014.02); *A61M 2202/064* (2013.01)

(58) Field of Classification Search
CPC .......... A61M 15/0021; A61M 16/0048; A61M 16/0488; A61M 16/049; A61M 16/0493; A61M 2210/0625; A61M 2210/1025; A61M 11/003; A61M 15/0023; A61M 15/0026; A61M 15/0028; A61M 15/003; A61M 15/0035; A61M 15/0041; A61M 2202/064; A47G 19/22; A47G 19/2205; B65D 43/163; B65D 43/16; B65D 2251/0003; B65D 222/545; B65D 222/556; B65D 21/064; B65D 43/169; B65D 43/161; B65D 51/18; B65D 2251/1083; B65D 2251/0021; B65D 2251/0047; B65D 2251/0068–009; B65D 47/08–0895; B65D 83/40
USPC ............................................ 220/254.1–254.6
See application file for complete search history.

(56) References Cited

U.S. PATENT DOCUMENTS

| | | | | |
|---|---|---|---|---|
| 5,071,033 A | * | 12/1991 | Siwek | B65D 83/0409 221/229 |
| 6,240,930 B1 | * | 6/2001 | Yuhara | A45C 13/008 206/235 |
| 7,351,215 B1 | * | 4/2008 | Roberts | A61H 19/34 601/72 |
| 9,095,198 B2 | * | 8/2015 | Apodaca | A45D 33/16 |
| 10,195,373 B2 | * | 2/2019 | Althorpe | A61M 15/0041 |
| 10,556,069 B2 | * | 2/2020 | Bhide | A61M 15/0026 |
| 11,020,549 B2 | * | 6/2021 | Ahern | A61M 15/002 |
| 2007/0102391 A1 | * | 5/2007 | Hoepner | B65D 47/0885 215/235 |
| 2008/0105256 A1 | | 5/2008 | Lulla et al. | |
| 2008/0173324 A1 | * | 7/2008 | Washington | A45D 33/24 132/294 |
| 2008/0257376 A1 | * | 10/2008 | Pires | A45D 40/24 132/294 |
| 2009/0205656 A1 | * | 8/2009 | Nishibayashi | A61M 15/0026 128/203.15 |
| 2010/0192949 A1 | * | 8/2010 | Wright | A61M 15/0093 128/203.15 |
| 2013/0255679 A1 | | 10/2013 | Andrade et al. | |
| 2013/0284202 A1 | * | 10/2013 | Limongi | B65D 5/5213 132/316 |
| 2014/0318538 A1 | * | 10/2014 | Bilgic | A61M 15/0028 128/203.15 |
| 2015/0059747 A1 | * | 3/2015 | Von Schuckmann | A61M 15/0026 128/203.15 |
| 2016/0279355 A1 | * | 9/2016 | Malhotra | A61M 15/0035 |
| 2017/0056608 A1 | * | 3/2017 | McDerment | A61M 15/0091 |

FOREIGN PATENT DOCUMENTS

| | | |
|---|---|---|
| SE | 1550964 A1 * | 12/2016 |
| WO | 2012/047181 A1 | 4/2012 |
| WO | 2012/047182 A2 | 4/2012 |
| WO | 2013/095311 A1 | 6/2013 |
| WO | 2015/128789 A1 | 9/2015 |

* cited by examiner

DEVICE FOR INHALING POWDERY SUBSTANCES

CROSS REFERENCE TO RELATED APPLICATIONS

This application is the National Stage of PCT/EP2017/070342 filed on Aug. 10, 2017, which claims priority under 35 U.S.C. § 119 of German Application No. 20 2016 104 666.1 filed on Aug. 25, 2016; German Application No. 20 2017 100 316.7 filed on Jan. 20, 2017; and German Application No. 20 2017 102 334.6 filed on Apr. 20, 2017, the disclosures of which are incorporated by reference. The international application under PCT article 21(2) was not published in English.

FIELD OF TECHNOLOGY

The invention relates to a device for inhaling powdery substances contained in capsules, comprising a housing, a capsule receiver, a closing cover and a mouthpiece, wherein a closure cap is provided, which is designed to simultaneously cover the mouthpiece, the closing cover and the capsule receiver, wherein the closure cap, the mouthpiece and the closing cover are further hinged in a pivotable manner, wherein two pivot axes, which are different but run in the same direction, are formed, namely a first pivot axis and a second pivot axis, which, in respect of a side view in which geometric axes of the pivot axes are represented in the form of points, are arranged next to each other and on a same side of the capsule receiver, wherein, in a use state of the device, the first pivot axis is further arranged closer to the capsule receiver, the closing cover and the mouthpiece can be pivoted about the first pivot axis, and only the closure cap can be pivoted about the second pivot axis.

The invention further relates to a device for inhaling powdery substances contained in capsules, comprising a housing, a capsule receiver, a closing cover and a mouthpiece, wherein a closure cap is provided, which is designed to simultaneously cover the mouthpiece, the closing cover and the capsule receiver, wherein the closure cap, the mouthpiece and the closing cover are further hinged in a pivotable manner, wherein two pivot axes, which are different but run in the same direction, are formed, namely a first pivot axis and a second pivot axis, which, in respect of a side view in which the geometric axes of the pivot axes are represented in the form of points, are arranged next to each other and on a same side of the capsule receiver, wherein, in a use state of the device, the first pivot axis is further arranged closer to the capsule receiver.

PRIOR ART

Such a device is initially known from WO 2012/047182 A2. The mouthpiece thereby has two pivot axes, which are arranged one below the other in the mentioned side view, when a receiving direction for the capsule receiver corresponds to a vertical. The closing cover is hinged to the thus upper pivot axis, and the mouthpiece and the capsule receiver are hinged together to the housing on the thus lower pivot axis. One of the pivot axes is fixedly formed on the housing and the other one so as to be pivotable about this pivot axis, which is fixed to the housing, with the capsule receiver and the mouthpiece.

With regard to the prior art, reference is to further be made to WO 2015/128789 A1. In the case of the device for inhaling powdery substances known therefrom, two pivot axes are also provided, which are arranged next to each other in the mentioned side view and in an orientation, in the case of which the receiving direction of the capsule receiver runs vertically. The closure cap and the mouthpiece are arranged on the thus outer pivot axis so as to be pivotable about the same axis, and only the closing cover, which is formed here together with the capsule receiver and which can be pivoted, is arranged on the inner pivot axis, which is arranged closer to the capsule receiver.

Finally, it is known from US 2013/255679 A1 to provide, in the case of such a device, a pivot axis, which is formed so as to be integrated on the housing and about which the closure cap is pivotally moveable, though providing a part, which can be equated with the closing cover, on a plug-in part for plugging into the housing. The mouthpiece is hinged in a pivotable manner to the plug-in part, in the area of the closing cover.

SUMMARY OF THE INVENTION

Based on the specified prior art, the invention is based on the object of further developing a device for inhaling powdery substances, as it has been specified above, in such a way that a good accessibility of the parts in the pivoted-open state is at hand during advantageous use by a user.

This object is initially solved by a device for inhaling powdery substances, whereby the focus is on that the closure cap, the mouthpiece, and the closing cover are each hinged so as to be pivotable about a pivot axis, which is fixedly mounted to the housing, and both pivot axes are formed on the housing so as to be immovable relative to one another. Both pivot axes are thus fixedly mounted to the housing.

This object is also solved by a device in which the closing cover and the closure cap can be pivoted about the second pivot axis and that only the mouthpiece can be pivoted about the first pivot axis, which is mounted to an upper side of the closing cover. In particular the mouthpiece can be pivoted freely.

It is also preferred that only two pivot axes are formed on the device. In a further development, however, three pivot axes can be provided as well, wherein the closure cap and the closing cover are each hinged directly to a pivot axis, and the mouthpiece is hinged in a pivotable manner to a pivot axis formed on the closing cover. The pivot axes, about which the closure cap and the closing cover can each be pivoted individually, are thus different pivot axes. The further, third pivot axis, together with the closing cover, can be provided in a pivotable manner.

The capsule receiver preferably also comprises a handle, which is further preferably movable in a slider-like manner, and needles, by means of which a capsule inserted into the capsule receiver can be opened by means of piercing. The needles are preferably connected to the handle for the joint movement.

It is provided in further preferred embodiment that, in respect of the mentioned side view, in which the geometric axes of the pivot axes are represented in the form of points, the mouthpiece and the closure cap extend towards each other without overlap in a most open position in respect of their outer contour. In the most open position, the farthest pivot position of the closure cap and of the mouthpiece, in particular the mouthpiece is completely visible for the user. A nesting of the mouthpiece in the open closure cap is not at hand.

The mouthpiece and the closing cover are preferably formed so as to be lockable with each other. In response to a common pivoting open of the mouthpiece, the closing cover can simultaneously be pivoted open as well. Insofar as the closing cover is formed so as to be pivotable relative to a capsule receiver, which is arranged to be pivotable as well, it can also be provided that the closing cover can be locked with the capsule receiver as well. The locking action to the mouthpiece can thereby preferably be formed to be stronger than a locking action to the capsule receiver. By pivoting open the mouthpiece, for inserting for instance a new capsule, the capsule receiver is not simultaneously pivoted open as well in such a case. In particular when the capsule can be readily inserted through the closing cover, which is not pivoted open, after pivoting open the mouthpiece, thus when the closing cover is not provided for instance with a screen, as is generally possible, it is preferred that the locking action of the closing cover to the capsule receiver is greater than to the mouthpiece. Even if, however, as is further possible and as is also preferred in many cases, a corresponding screen is provided but is connected to the mouthpiece, it is preferred that the locking action of the closing cover to the capsule receiver is greater than to the mouthpiece, so that the user only pivots open the mouthpiece in order to be able to insert a new capsule.

The closing cover can also be formed in one piece or quasi in one piece (operationally not easily or readily releasable) with the capsule receiver. A user-side pivoting open of the closing cover then regularly also leads to a pivoting open of the capsule receiver.

However, an independent ability to lock the capsule receiver with the housing can also be provided for this purpose. The totality of closing cover and capsule receiver can be locked only via an ability to lock the capsule receiver with the housing or only via an ability to lock the closing cover with the housing. In such a case, a further ability to lock can be formed between the closing cover and the capsule receiver. Due to a different adjustment of the opening force between the closing cover and the capsule receiver, it can be adjusted whether by pivoting the closing cover upwards, the capsule receiver also simultaneously pivots upwards or whether the capsule receiver regularly remains in the housing and only upon immediate action on the capsule receiver, the opening force, which is then stronger, can be exerted to release the locking between the capsule receiver and the housing, in order to jointly pivot the closing cover and the capsule receiver.

In further embodiment, the closing cover and/or the mouthpiece can be plug-connected to the housing or, in the case of the mouthpiece, alternatively to the closing cover. The plug connection can refer solely or at least preferably to the fixation of the closing cover and/or of the mouthpiece in the area of the respective pivot axis. According to a possible embodiment, the pivot axis can be formed only by obtaining the plug connection between the closing cover and/or the mouthpiece and the housing or, in the case of the mouthpiece, between the mouthpiece and the closing cover. For this purpose, the parts, which can be plug-connected to each other, preferably each have portions of the pivot axis, which is at hand in the use state of the device.

The possible plug connection turns out to in particular be advantageous in terms of manufacturing technology. In the case of a preferred embodiment of the parts as plastic injection molded parts, the respective axis portions of the parts, which can be plug-connected to each other, can also be formed directly as part of the plastic injection molding process.

The closing cover can thus have integrally molded journals, for the plug reception in plug moldings of the housing or the housing can have integrally molded journals for the plug reception in plug moldings of the closing cover. In respect of a cross section at right angles to the orientation of the geometric pivot axis, the plug moldings can be formed so as to engage over the journal in a clamp-like manner, wherein areas of the plug moldings preferably provide for a radial, flexible escape in respect of the geometric axis, so as to thus establish the plug-and-locking connection after over-travelling and catching the journal.

In a possible embodiment, the closing cover is thus plug-connected to the housing and the mouthpiece to the closing cover.

A deformation tendency results in respect of the plug moldings as part of the insertion process. In a possible embodiment, said deformation tendency can be prevented in particular in the use state of the device, i.e. in particular in the closed position of the closing cover. In contrast to the deformation tendency resulting in response to the insertion process, the plug moldings of the housing in the use state of the device can be encompassed or affected by an area of the closing cover for this purpose. The plug connection can thus not be released in particular in the use position of the closing cover, for example. The respective plug moldings cannot escape to release the received journals, because they are blocked by an area of the closing cover in particular on the outer wall side.

In a preferred embodiment, an orientation of the closing cover relative to the housing, which does not correspond to the use state, is thus necessary between closing cover and housing to obtain the plug connection in particular between closing cover and housing.

The journal can be formed in a cross section comprising an annular wall. The journal can thus be formed as hollow journal. Such an embodiment provides advantages in particular with regard to obtaining the plug connection in cooperation with the plug molding, which receives or encompasses the journal, respectively.

The closing cover can have a plug molding for a pivot axis of the mouthpiece. In the alternative, the mouthpiece can have a plug molding for a journal of the closing cover. Closing cover and mouthpiece can thus be plug-connected to each other, further in particular to form a joint pivot axis, about which the mouthpiece and, preferably independently thereof, the closing cover, can be pivoted out of a use position or into it, respectively, relative to the housing.

The plug directions for obtaining the plug connections between the closing cover and the housing on the one hand, and the mouthpiece and the closing cover on the other hand, can draw an acute or right angle to one another, projected into a plane perpendicular to the geometric pivot axis of the closing cover, in the circumferential direction to the geometric pivot axis. In a possible embodiment, the plug direction to obtain the plug connection between the closing part and the housing can thus be selected approximately perpendicular to a surface extension of the closing cover (in respect of the use position), while the plug direction for obtaining the plug connection between the mouthpiece and the closing cover can, for example, be selected essentially perpendicular to a cross sectional surface of the closing cover, in which cross sectional surface the geometric pivot axis is represented as line.

The angle between the two plug directions can be, for example, 30 degrees up to 90 degrees, thus further for example also 45 or 65 degrees, but additionally also less than 30 degrees, for example up to 20 or 15 degrees.

BRIEF DESCRIPTION OF THE DRAWINGS

The invention is described below by means of the enclosed drawing, which, however, only represents exemplary embodiments. A part, which is described only in respect of one of the exemplary embodiments and which, in the case of a further exemplary embodiment, is not replaced by a different part due to the special feature emphasized therein, is thus also described as at least a possible part, which is present, for this further exemplary embodiment. On the drawing.

DESCRIPTION OF THE EMBODIMENTS

Figure 1:
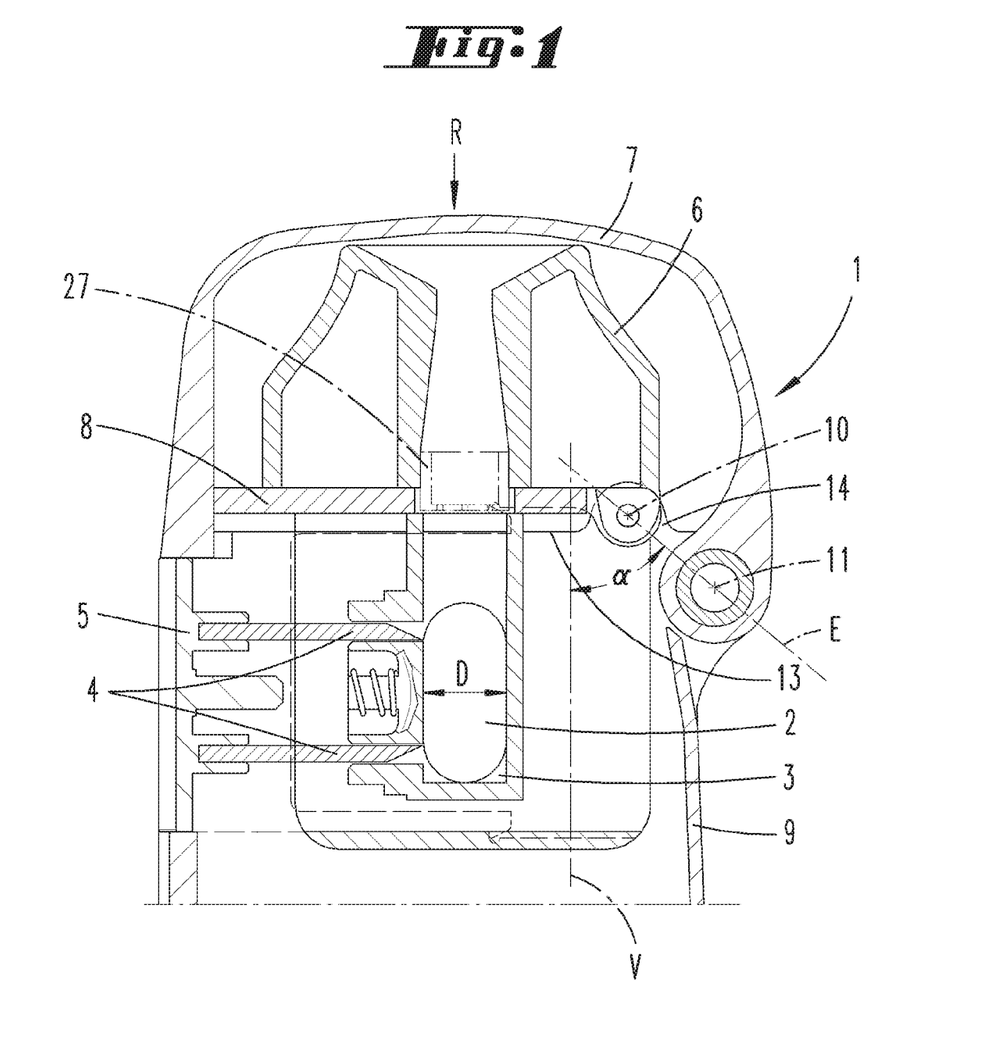
FIG. 1 shows a cross sectional view of the device for inhaling in the closed state, relating to a first embodiment.

What is illustrated and described with reference to FIG. 1 is a device 1 for inhaling powdery substances. The powdery substances are thereby contained in capsules 2, which can be received in a capsule receiver 3 of the device. The capsules 2 can be pierced by means of needles 4 by operation on a handle 5. In response to the user subsequently sucking on a mouthpiece 6, he can thereby inhale the pharmaceutical substance contained in the capsules 2.

Figure 10:
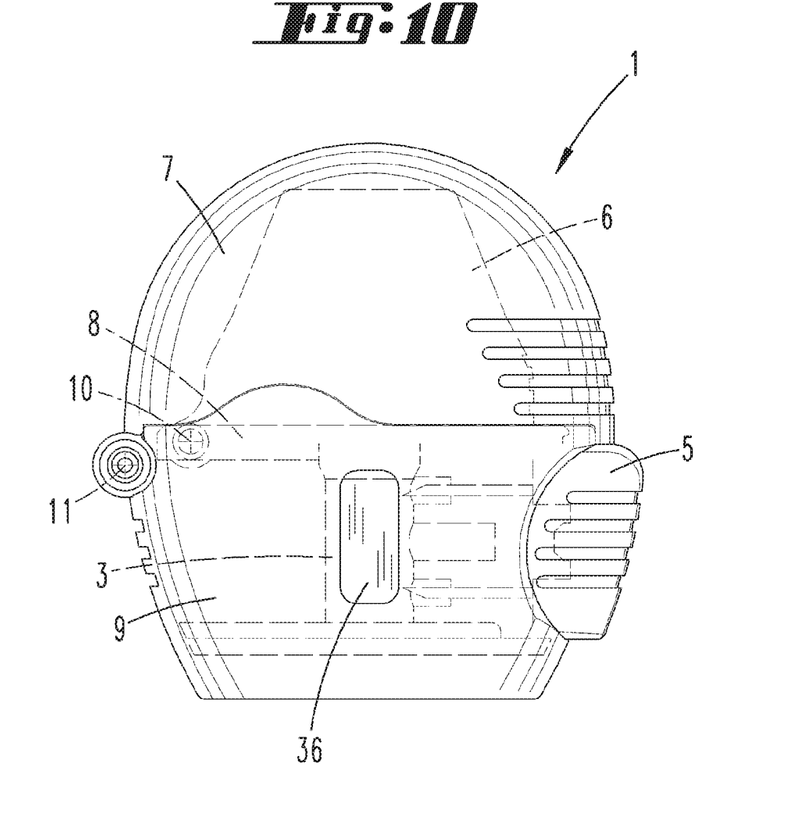
FIG. 10 shows the device in a further embodiment in the closed state.
Figure 11:
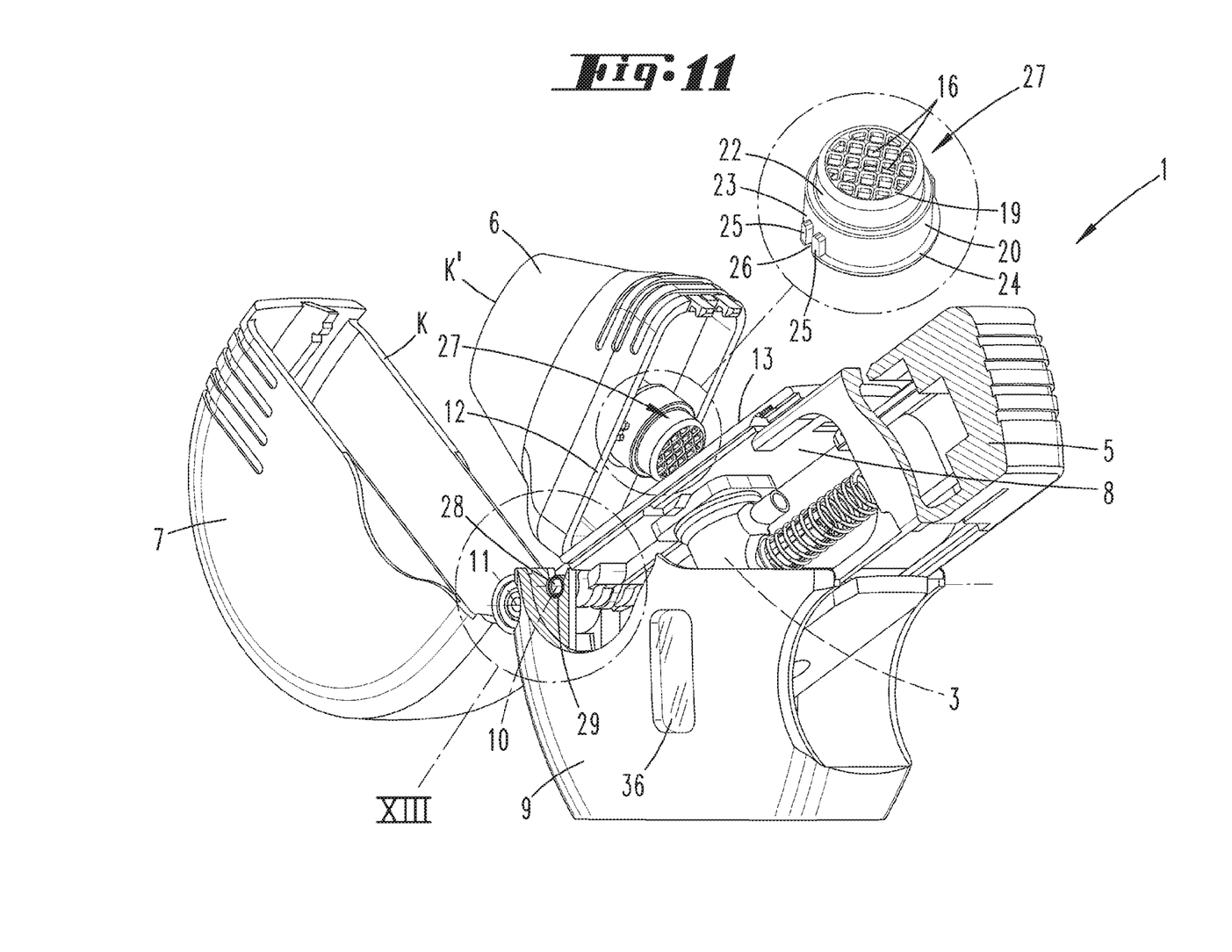
FIG. 11 shows the device according to FIG. 10 in partially cut perspective illustration, relating to the open state of the device.

It can be controlled, whether a capsule 2 is located in the capsule receiver 3 through a viewing window 36, which may be provided on the housing side, as it is illustrated in an exemplary manner in FIGS. 10 and 11.

The device 1 further has a closure cap 7, which in the closed state of the device, as illustrated in FIG. 1, covers the mouthpiece 6. Below the mouthpiece, the device also has a closing cover 8. The closing cover 8 can be formed to be fixedly connected, at least in a rotationally fixed manner, to the capsule receiver 3.

The closure cap 7, the mouthpiece 6, and the closing cover 8 are pivotably hinged to a—lower—housing 9. For this purpose, two different pivot axes are formed, namely a first pivot axis 10 and a second pivot axis 11.

The pivot axes 10 and 11 are preferably formed—at least across a part of the width of the device—as real axis parts or journals, which are received in corresponding receptacles, in particular eye-like receptacles, for the pivotable mobility. The receptacles are thereby preferably formed in the housing 9 or also on the other part in respect of one of the parts mouthpiece 6 or closing cover 8.

The axes 10 and 11 further each have a geometric axis, which is suggested in the drawing by means of a cross and which runs though the center of the real axes 10 and 11 illustrated here.

In the mentioned cross sectional view of FIG. 1, for example, which corresponds to a side view, in which the mentioned geometric axes of the pivot axes 10, 11 are represented in the form of points, the axes 10 and 11 are located next to each other. They are not necessarily located—in respect of the mentioned illustration, in which an insertion direction R for the capsule receiver corresponds to a vertical—in a plane, which runs at right angles to the mentioned insertion direction R and which would correspond here to a horizontal. In fact, they are preferably arranged differently in the vertical direction, wherein the outer, second pivot axis 11 is more preferably arranged lower than the inner, first pivot axis 10. In the illustration as line resulting here, a plane E through the pivot axes 10, 11 in FIG. 1 thus draws an acute angle α with a vertical V. In its orientation in the Figures, the vertical V corresponds to the insertion direction R. The angle α can be, for example, between 0 and 30°. The variety of the arrangement in the vertical direction, however, is preferably small, preferably corresponds only to one-half to one-twentieth of a largest free horizontal dimension D of the capsule receiver 3, for instance with regard to the vertical distance (in respect of a vertical distance between a horizontal drawn in each case through the first pivot axis 10 and the second pivot axis 11).

Together, the closing cover 8 and the mouthpiece 6 can be pivoted about the first pivot axis 10, and the closure cap 7 can solely be pivoted about the second pivot axis 11.

Figure 2:
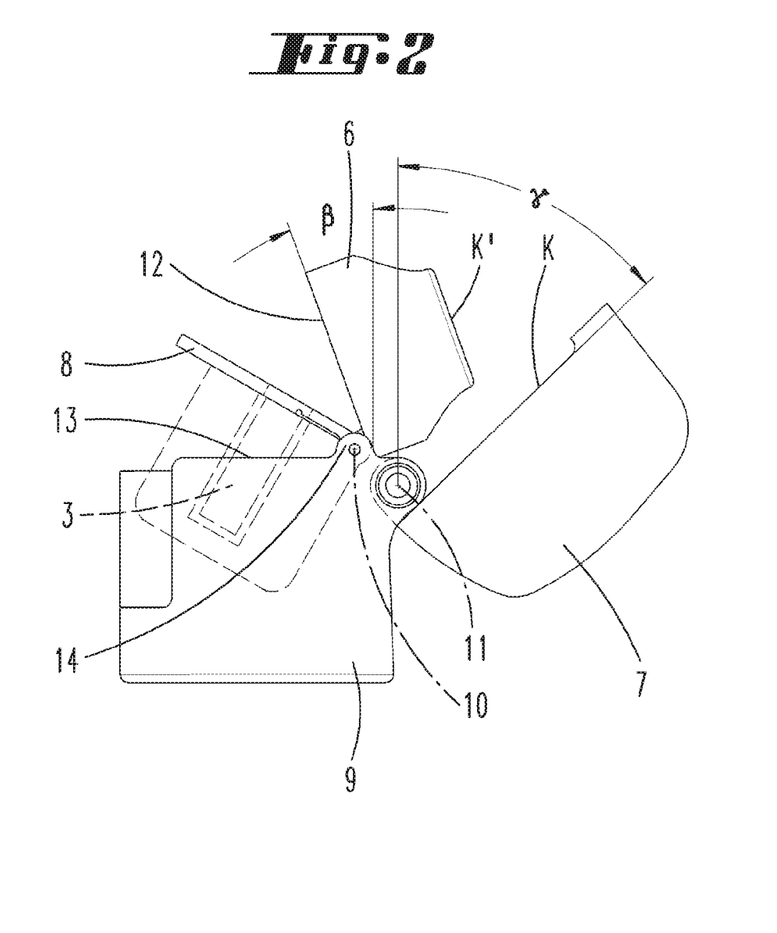
FIG. 2 shows an uncut side view of the device according to FIG. 1 in the open state.

A pivoted open position of the parts can be seen in FIG. 2.

It is preferably at hand thereby and as is illustrated as well that the mouthpiece 6 and the closure cap 7 extend relative to each other without an overlap in a most open position in respect of their outer contour K or K', respectively. The pivoted open position of the mouthpiece 6 can thereby be at hand in such a way that an outer edge 12, which is assigned to the closing cover 8 and which more preferably runs in an approximately continuous straight line, runs according to a vertical in the maximally pivoted open state (in respect of the illustration according to FIG. 1) or draws an acute angle β with the vertical, respectively, for instance an angle of between 1 and 30°.

As can be seen and as is preferred, in contrast, the corresponding outer edge of the closing cover 8 in the mentioned open position draws a second, preferably larger, acute angle γ between 0 and 45° with a vertical. While the first acute angle β can be at hand on both sides of the vertical in the maximum pivot-open position of the mouthpiece 6, the second acute angle γ of the closing cover with the vertical in the maximum open state of the closing cover 7 is only at hand in respect of the side of the vertical facing away from the capsule receiver.

As illustrated in the case of the exemplary embodiment, the first pivot axis 10 can further be received in a bearing molding 14, which protrudes upwards, in respect of an upper edge 13 of the housing 9. The spreading in the open position according to FIG. 2 or FIG. 11 can be obtained in an even more advantageous manner thereby.

The mouthpiece 6 and the closing cover 8 can be locked with each other. In a position, in which they are locked with each other, they can be pivoted together. As also described further above in particular in one of the embodiments, the closing cover 8 and the capsule receiver 3 can further be connected to each other for a joint pivoting.

Figure 3:
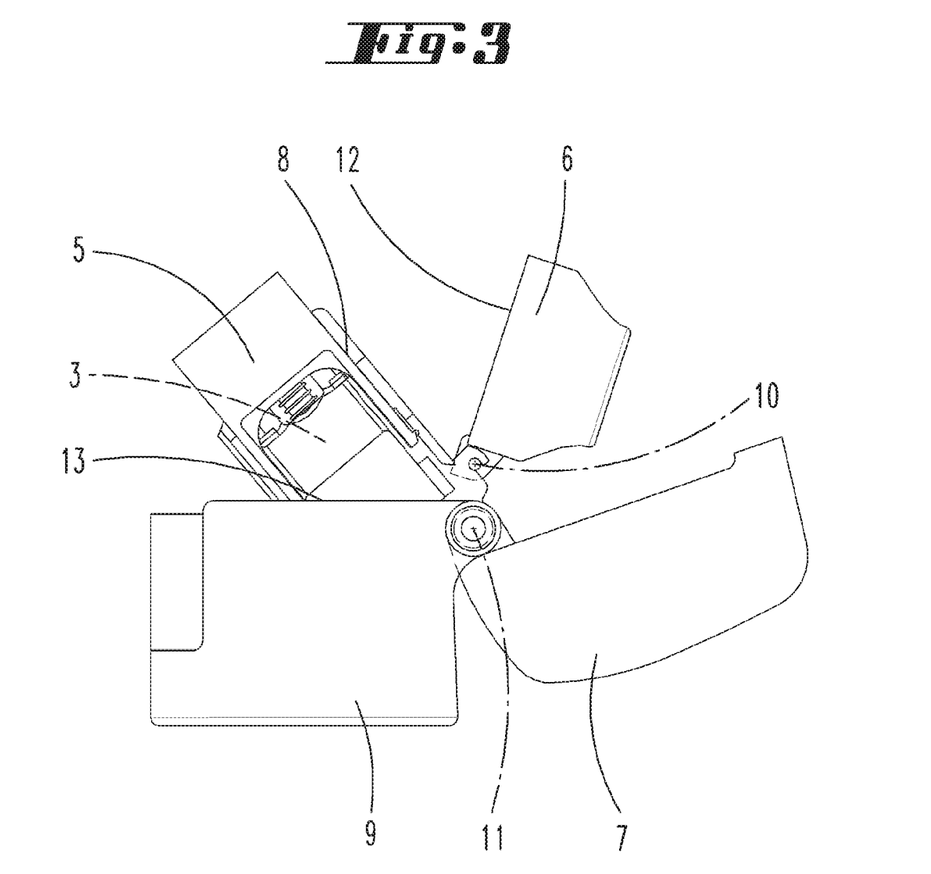
FIG. 3 shows a further embodiment, in the case of which the closing cover and the closure cap can be pivoted about a joint second pivot axis on a joint, second pivot axis, and the mouthpiece can be pivoted on a first pivot axis formed on the closing cover, in the open state.

In respect of FIG. 3, a further embodiment is illustrated, in the case of which the second pivot axis 11 is a joint pivot axis for the closing cover 8 and the closure cap 7, while the first pivot axis 10 is attached to an upper side of the closing cover 8, and only the mouthpiece 6 can be pivoted about this first pivot axis 10. It thus results thereby that, insofar as it is also in correspondence with the first embodiment, the mouthpiece 6 and the closing cover 8 can also be pivoted together in combined, preferably locked form. In the case of the embodiment of FIG. 3, the joint pivotability of the closing cover and of the mouthpiece 6 about the second pivot axis 11 is at hand. It also further follows that in the completely pivoted open state, as it is illustrated at least in respect of the mouthpiece 6 and the closure cap 7, but preferably also with regard to the closing cover 8 in FIG. 3, the complete separation according to contour between the closure cap 7 and the mouthpiece 6 can result thereby as well.

With regard to further details regarding the separation according to the contour, reference is also made to the description of the first exemplary embodiment.

Figure 4:
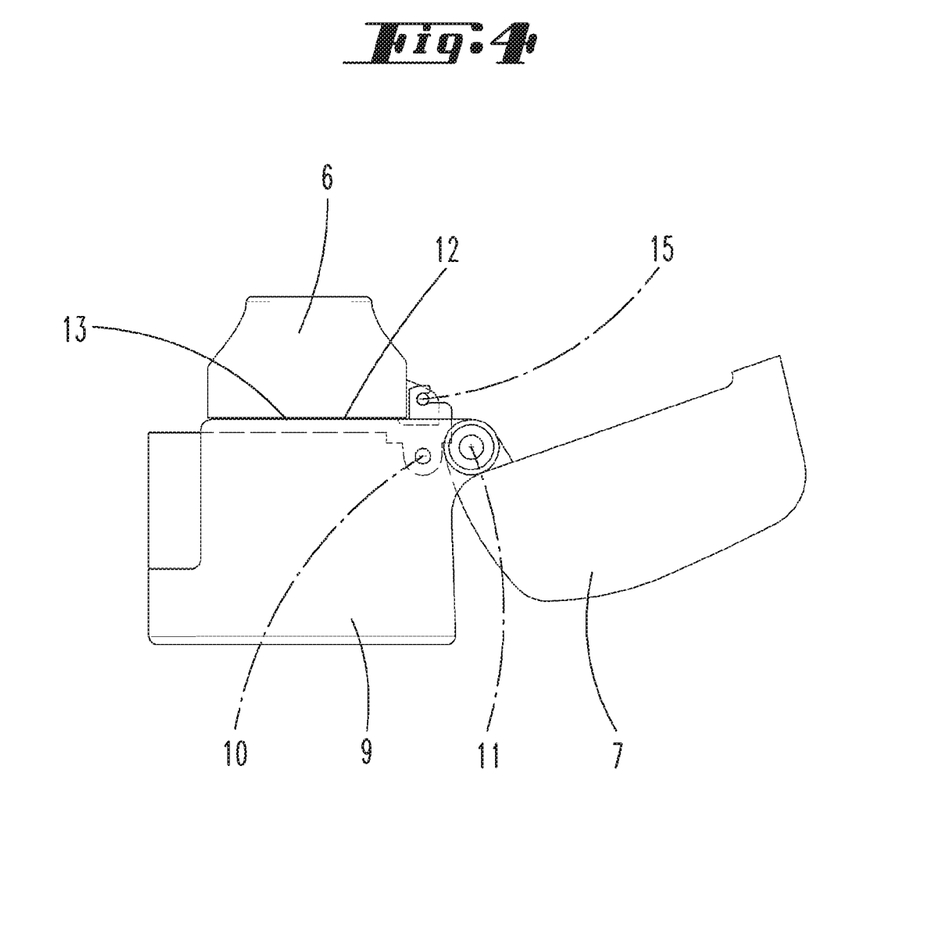
FIG. 4 shows a further embodiment, in the case of which, according to FIG. 1, the closing cover and the closure cap are hinged to two different pivot axes fixedly mounted to the housing, and the mouthpiece can be pivoted about a further pivot axis formed on the closing cover, in the closed state.
Figure 5:
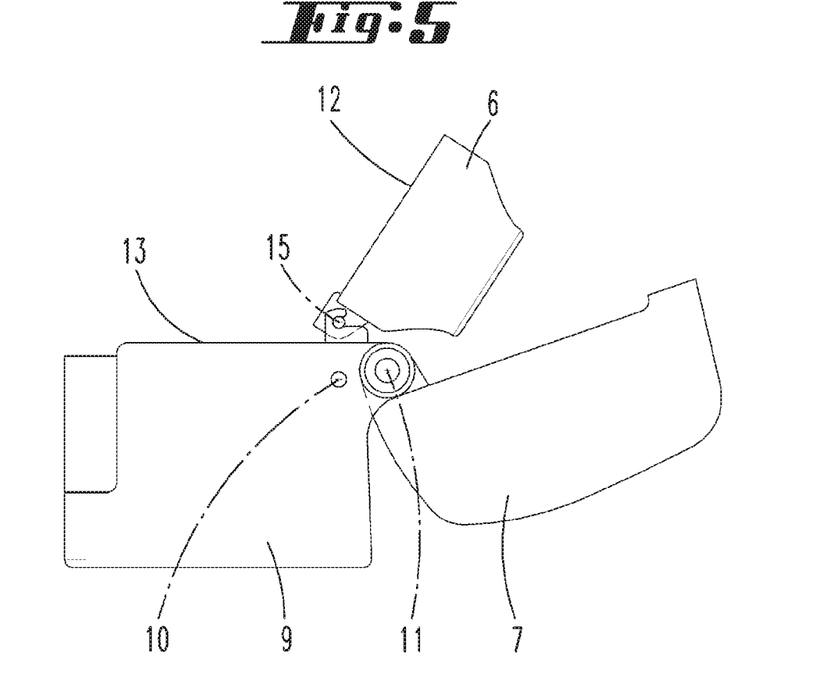
FIG. 5 shows an illustration of the device according to FIG. 4 comprising pivoted open mouthpiece and closure cap.
Figure 6:
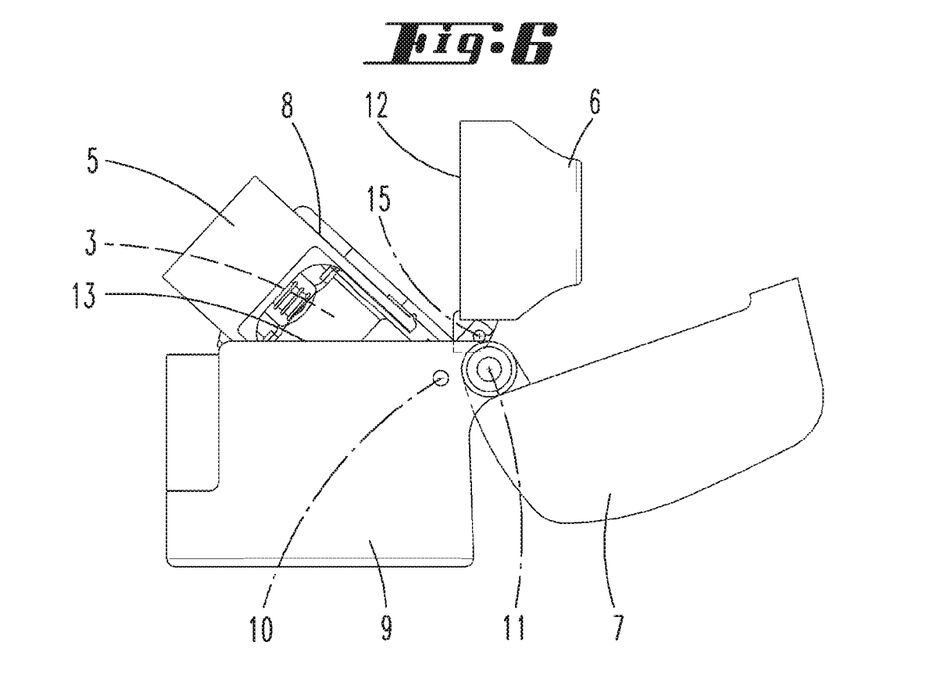
FIG. 6 shows an illustration according to FIG. 5, in which the closing cover is pivoted open as well.

In respect of FIGS. 5 to 6, a further embodiment is illustrated once again, which correspond to the first embodiment of FIGS. 1 to 2 with regard to the first pivot axis 10 and the second pivot axis 11. Contrary to the illustrations of the embodiments of FIGS. 1 and 2, however, the first pivot axis 10 can be arranged lower, preferably slightly lower, than the second pivot axis 11 in the case of this embodiment. On the other hand, however, this embodiment can also be realized in the case of the embodiment of FIGS. 1 and 2. Vice versa, the same relationships as described in the case of the first embodiment result with regard to the vertical distance in the case of the embodiments of FIGS. 4 to 6 of the first and second pivot axis.

The closing cover 8 is further also formed here with a separate, but in this case a third, pivot axis 15, for the mouthpiece 6.

It is further a special feature that the mouthpiece 6 can be removed from the receiver for the third pivot axis by means of unlocking. On principle, the same is additionally also possible in all of the embodiments described here for the first and/or second pivot axis.

Figure 7:
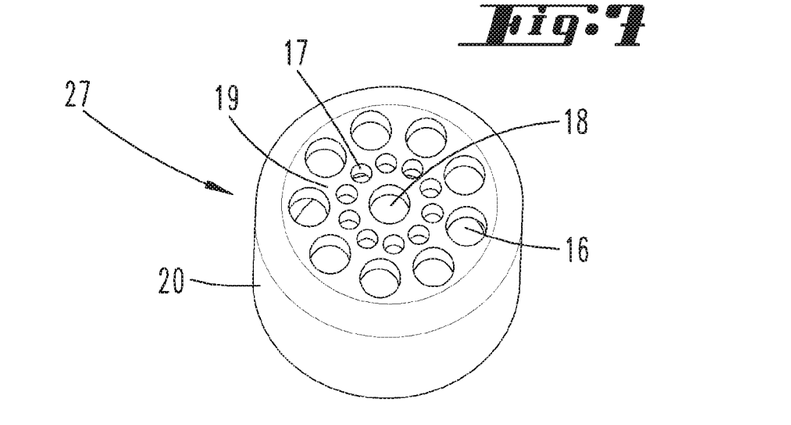
FIGS. 7-9 show an illustration of different screen alternatives.
Figure 8:
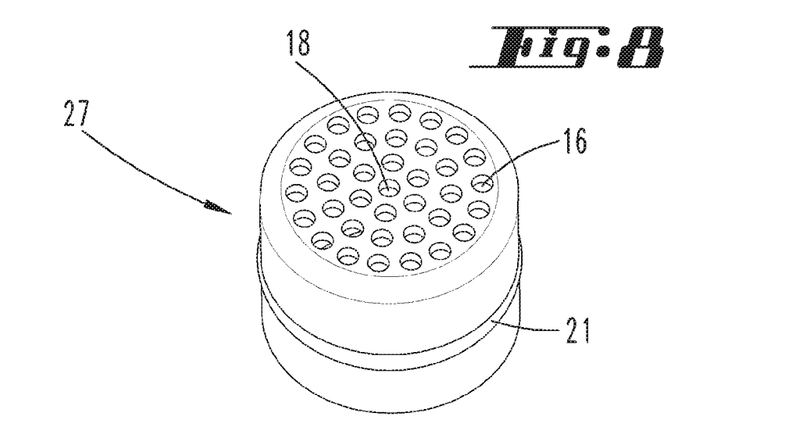
Figure 9:
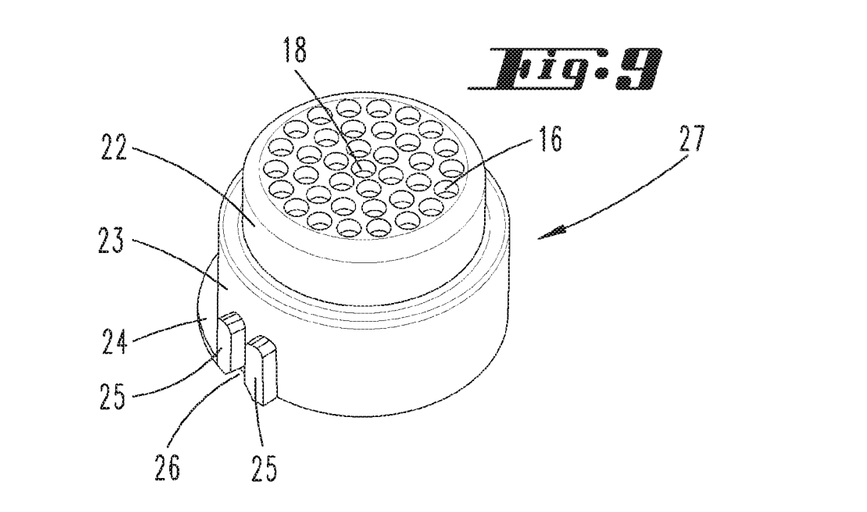

In respect of FIGS. 7 to 9 (further also in FIG. 11), different embodiments for a screen 15 are illustrated. In respect of all embodiments, a screen 15 can be arranged in the mouthpiece in the manner suggested in FIG. 1.

In the case of the embodiment of FIG. 7, the screen 15 has two coaxial rims of holes 16 and 17. The holes 16, which are preferably arranged externally to the holes 17, are thereby provided with a larger diameter. The diameter of a hole 17 preferably corresponds to two-thirds or less, up to approximately one-fourth, of a diameter of the hole 16.

A central individual hole 18 is further provided. The hole 18, in turn, preferably has a larger diameter than the holes 17. More preferably, the diameter of the hole 18 corresponds to that of a hole 16.

In the case of the embodiment of FIG. 8, such holes are provided in respect of three concentric circular lines, wherein all of the holes 16 of the embodiment of FIG. 8 more preferably have an identical diameter. This also includes a central hole 18.

In respect of the holes, the embodiment of FIG. 9 preferably corresponds to the embodiment of FIG. 8.

The holes 16 according to the embodiments illustrated in FIG. 11 can also have outlines, which are rectangular, all the way to square, more preferably of the same size.

Such a screen part 27 is further formed with a pot bottom 19 and a pot wall 20.

In the case of the embodiment of FIG. 8, the pot wall 20 is provided a circumferential bead 21, approximately in the center of its wall height. The bead 21 runs externally on the pot wall 20. An advantageous pressing and holding in the mouthpiece can be obtained thereby.

In the case of the embodiment of FIG. 9, the pot wall is formed in a staggered manner. Starting at the pot bottom, a first pot wall section 22 and a second pot wall section 23 adjoin. The diameter of the second pot wall section 23 is larger than the diameter of the first pot wall section 22.

On its free end facing away from the pot bottom 19, the pot wall 20 or 22, 23 can further have a section 24, which projects to the outside across a part of its circumference (see also FIG. 11). The section 24 serves for the advantageous holding in the mounted state. An insertion groove 26 can further also be formed on the pot wall, for instance by means of vertically running ribs 25. This is in particular advantageous with regard to a directed installation of the screen into the mouthpiece. On the mouthpiece side, a corresponding protrusion can then be formed, which engages with the groove 26.

FIGS. 10 to 16 show a further embodiment of the device 1, in the case of which the closing cover 8 is plug-connected to the housing 9, and the mouthpiece 6 to the closing cover 8. Closing cover 8 and mouthpiece 6 are held so as to be pivotably movable about a joint pivot axis 10, wherein the ability of the mouthpiece 6 to pivotably move about the pivot axis 10 can be independent from the ability of the closing cover 8 to pivotably move about the same pivot axis 10. However, a joint pivoting can furthermore be specified as well, for example in response to a further locking, as described, which may be capable of being released by the user.

In the illustrated exemplary embodiment, the plug connection is at hand by means of journals and thus plug-connectable plug moldings.

Journals 28, which point to the outside and protrude freely, are thus preferably integrally molded to the closing cover 8, each approximately on the end side of a longitudinal outer edge of the closing cover 8, for plug-reception in the plug moldings 29 of the housing 9. The plug moldings 29 are formed in the shape of pocket-shaped grooves, which are arranged on the housing wall inner side and which are designed so as to be open facing towards the upper edge 13 of the housing 9 and inwards, i.e. towards each other in respect of the pivot axis 10.

In respect of a cross section, in the case of which the geometric pivot axis 10 is represented in the form of points (see FIG. 14), a fork-shaped design of the plug molding 29 can be seen, comprising a groove base, which is formed in the shape of a segment of a circle and so as to be adapted to the journal 28 in terms of diameter in this cross section. The shape of a segment of a circle extends across a circumference of more than 180 degrees, so that the received journal 28 is captured in a captive manner in the plug connection position.

Figure 14:
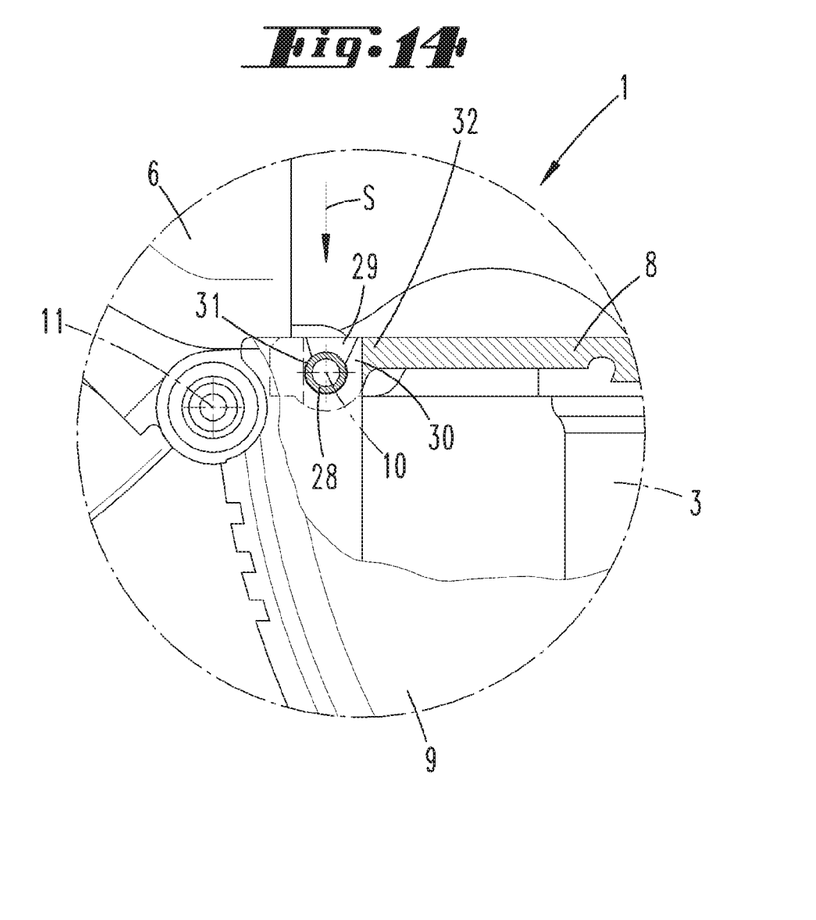
FIG. 14 shows the section according to line XIV-XIV in FIG. 13.
Figure 15:
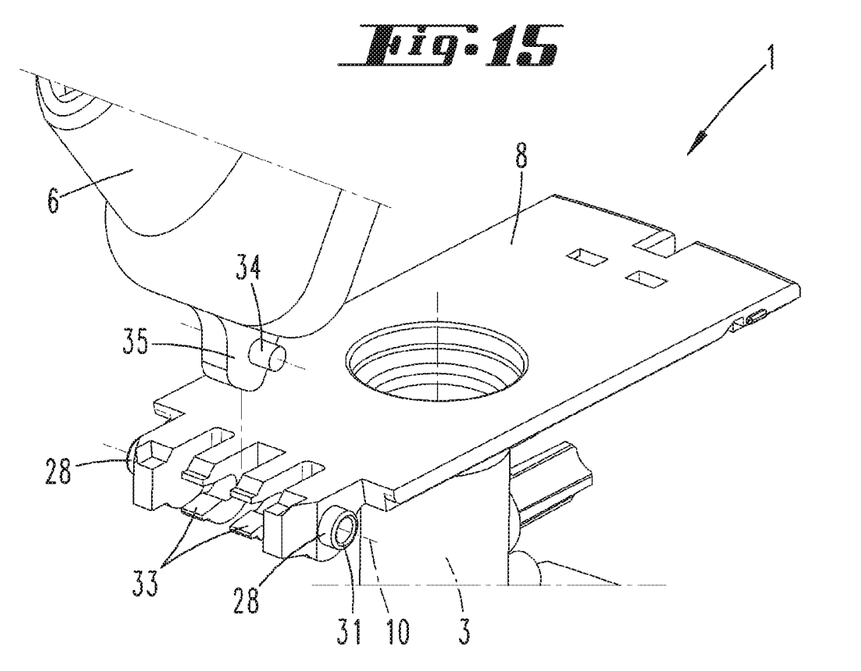
FIG. 15 shows the closing cover and the mouthpiece in perspective individual illustration.

Starting at the groove base in the shape of a segment of a circle, the plug molding 29 extends in the cross section so as to widen in a funnel-like manner all the way to the upper edge 13.

In particular the plug molding leg 30, which faces away from the closure cap pivot axis 11, can radially escape in a suitable manner as part of the plug connection, i.e. as part of the journal 28 dipping into the plug moldings 29, in order to obtain the rear grip position according to FIG. 14 in respect of the pivot axis 10.

As illustrated, the journal 28 can also form an annular wall 31. The latter is preferably elastically resilient, in particular due to the given properties of the preferred plastic material, which further leads to an advantageous plug-in process.

Figure 12:
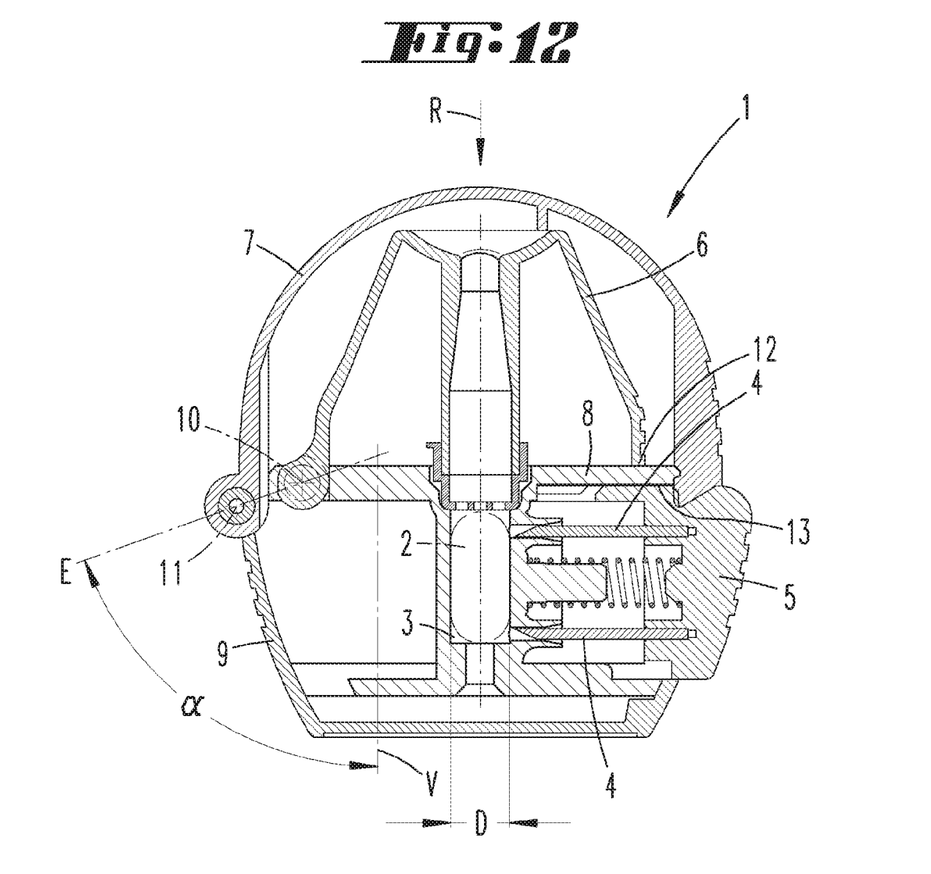
FIG. 12 shows the device in the closed state according to FIG. 1 in a cross sectional view.
Figure 13:
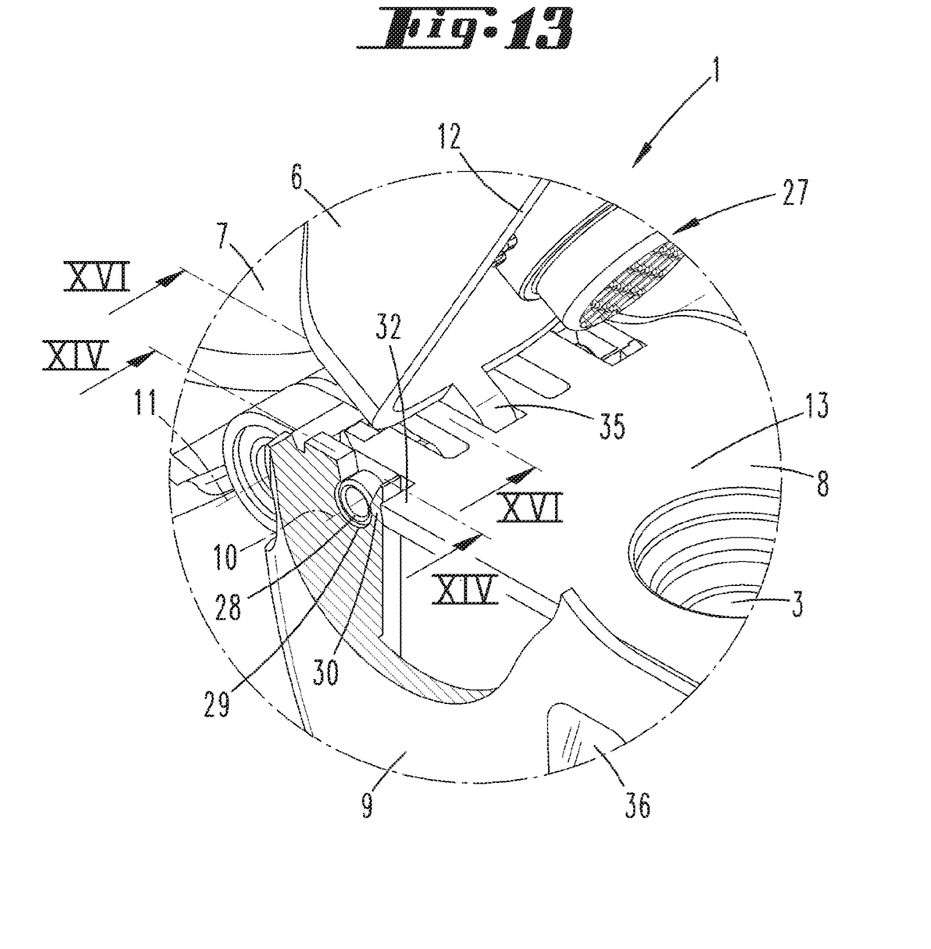
FIG. 13 shows the enlargement of the area XIII in FIG. 11 but with a closing cover pivoted in use position.

The closing cover 8 is preferably locked in place in a pivot position thereof, in which the closing cover 8 is located outside of the use state according to, for example, FIGS. 12 to 14, further for example in a position, which is pivoted open by approximately 90 degrees thereto in respect of a cross section.

In the pivoted-away position, corresponding to the common use position of the closing cover 8, the plug molding 29 of the housing 9, in particular the respective plug molding leg 30, contrary to a deformation tendency resulting in response to the plug-in process, is encompassed by an adjacent area 32 of the closing cover 8, which may even abut on the plug molding leg 30 in the use position, whereby the plug connection between closing cover 8 and housing 9 in the area of the pivot axis 10 in the use position is secured. In the use position, the plug molding leg 30 is thus prevented from an evasive movement.

Two fork-like plug moldings 33 are formed between the closing cover sections, which support the journals 28 facing axially to the outside, at a distance from these sections as well as to one another in the axial direction. A design approximately identical to the plug moldings 29 of the housing 9 essentially results thereby, even though an opening of the plug moldings 33 is at hand in the direction of the pivot axis 11 on the side of the closure cap.

Correspondingly positioned journals 34 of the mouthpiece 6, which are integrally molded on a correspondingly positioned cantilever arm 35, can be plugged into the plug moldings 33.

The plug moldings 29 of the housing 9, the journals 28 of the closing cover 8, as well as the plug moldings 33 thereof and the journals 34 of the mouthpiece 6 are centrally permeated jointly by the geometric pivot axis 10 in the plug connection position.

Figure 16:
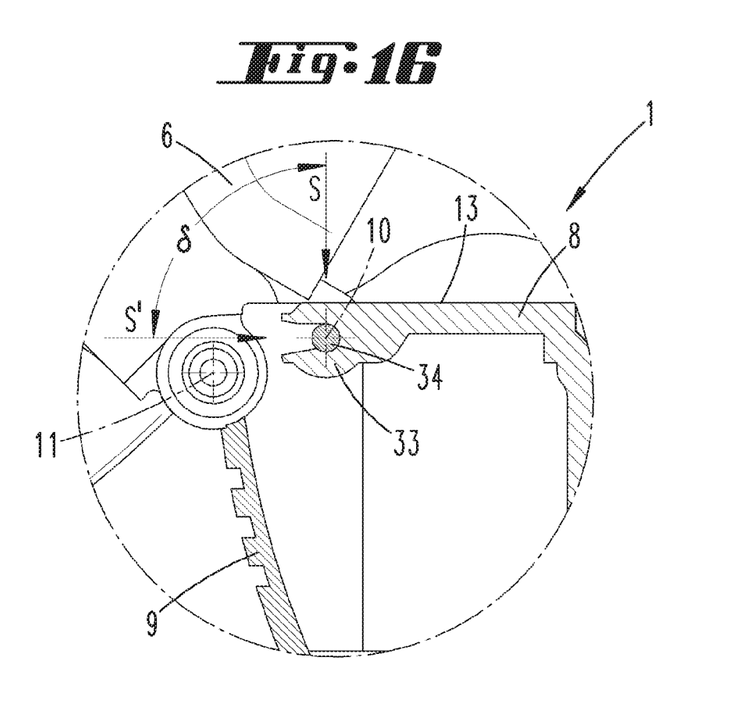
FIG. 16 shows the section according to line XVI-XVI in FIG. 13.

To obtain the respective plug connection, a plug direction S, S' is specified in each case. As can in particular be seen from the illustrations in FIGS. 14 and 16, the plug direction S for obtaining the plug connection between the closing cover 8 and the housing 9, and the plug direction S' for obtaining the plug connection between the mouthpiece 6 and the closing cover 8, projected into a plane perpendicular to the geometric pivot axis 10 (as it is illustrated in FIGS. 14 and 16) draw an acute up to a right angle δ to one another in the circumferential direction to the geometric pivot axis 10 (in particular in respect of the illustrated use position of the closing cover 8).

REFERENCE LIST

| | |
|---|---|
| 1 | device |
| 2 | capsule |
| 3 | capsule receiver |

REFERENCE LIST -continued

| | |
|---|---|
| 4 | needle |
| 5 | handle |
| 6 | mouthpiece |
| 7 | closure cap |
| 8 | closing cover |
| 9 | housing |
| 10 | pivot axis |
| 11 | pivot axis |
| 12 | outer edge |
| 13 | upper edge |
| 14 | bearing molding |
| 15 | pivot axis |
| 16 | holes |
| 17 | holes |
| 18 | holes |
| 19 | pot bottom |
| 20 | pot wall |
| 21 | bead |
| 22 | pot wall section |
| 23 | pot wall section |
| 24 | projecting section |
| 25 | ribs |
| 26 | groove |
| 27 | screen part |
| 28 | journal |
| 29 | plug molding |
| 30 | plug molding leg |
| 31 | wall |
| 32 | area |
| 33 | plug molding |
| 34 | journal |
| 35 | cantilever arm |
| 36 | viewing window |
| E | plane |
| D | dimension capsule receiver |
| K | outer contour |
| K' | outer contour |
| R | insertion direction |
| S | plug direction |
| S' | plug direction |
| V | vertical |
| α | acute angle |
| β | acute angle |
| γ | acute angle |
| δ | angle |

The invention claimed is:

1. A device for inhaling powdery substances contained in capsules, comprising a housing having a bottom and an upper opening, a capsule receiver, a closing cover, a mouthpiece, and a closure cap, the closure cap being designed to simultaneously cover the mouthpiece, the closing cover and the capsule receiver, wherein the closure cap, the mouthpiece and the closing cover are hinged in a pivotable manner, wherein two separate pivot axes, which run in a same direction, are formed, and comprise a first pivot axis and a second pivot axis, which, in respect of a side view in which geometric axes of the pivot axes are represented as points, are arranged next to each other and on a same side of the capsule receiver, wherein the first pivot axis is arranged closer to the capsule receiver than the second pivot axis in a use state of the device, wherein the closing cover and the mouthpiece are pivotable about the first pivot axis, and only the closure cap is pivotable about the second pivot axis, wherein the pivot axes are fixedly mounted to the housing and are immovable relative to one another, wherein the closing cover is directly plug-connected to the housing and the mouthpiece is directly plug-connected to the closing cover, wherein plug directions of the closing cover to the housing and of the mouthpiece to the closing cover are different from each other and enclose an acute or right angle when the plug directions are viewed projected into a plane perpendicular to a geometric pivot axis of the closing cover, in a radial direction to the geometric pivot axis, wherein the closing cover has integrally molded journals and integrally formed fork-shaped plug moldings, the housing has integrally formed fork-shaped plug moldings, the mouthpiece has integrally molded journals, wherein the closing cover's journals are in plug reception with the fork-shaped plug moldings of the housing, wherein the mouthpiece's journals are in plug reception with the fork-shaped plug moldings of the closing cover, and wherein the fork-shaped plug moldings of the closing cover are located between the journals of the closing cover and open in a direction substantially perpendicular to an axial extent of the journals of the closing cover.

2. The device according to claim 1, wherein the device has only two pivot axes which comprise the first pivot axis and the second pivot axis.

3. The device according to claim 1, wherein a third pivot axis, which is pivotable together with the closing cover, is formed on the closing cover.

4. The device according to claim 3, wherein only the mouthpiece is pivotable about the third pivot axis.

5. The device according to claim 1, wherein in respect of the side view, in which the geometric axes of the pivot axes are represented in the form of points, the pivot axes are positioned such that the mouthpiece and the closure cap extend towards each other without overlap of their outer contours in a most open position.

6. The device according to claim 1, wherein the mouthpiece and the closing cover are configured to be locked with each other for a joint pivoting.

7. The device according to claim 1, wherein the capsule receiver and the closing cover are connected to each other for a joint pivoting.

8. The device according to claim 1, wherein the plug moldings of the housing in the use state of the device are encompassed by an area of the closing cover.

9. The device according to claim 1, wherein each one of the journals of the closing cover and the mouthpiece has a cross section comprising an annular wall.

10. The device according to claim 1, wherein the fork-shaped plug moldings of each of the housing and closing cover have openings that widen toward a free end of each fork-shaped plug molding.

* * * * *